United States Patent [19]
Baust et al.

[11] Patent Number: 5,520,682
[45] Date of Patent: * May 28, 1996

[54] CRYOSURGICAL INSTRUMENT WITH VENT MEANS AND METHOD USING SAME

[75] Inventors: John G. Baust, Candor, N.Y.; ZhaoHua Chang, Poolesville; J. J. Finkelstein, Bethesda, both of Md.

[73] Assignee: Cryomedical Sciences, Inc., Rockville, Md.

[*] Notice: The portion of the term of this patent subsequent to Sep. 6, 2011, has been disclaimed.

[21] Appl. No.: 401,035

[22] Filed: Mar. 6, 1995

Related U.S. Application Data

[63] Continuation of Ser. No. 137,353, Oct. 18, 1993, abandoned, which is a continuation-in-part of Ser. No. 756,287, Sep. 6, 1991, Pat. No. 5,254,116.

[30] Foreign Application Priority Data

Sep. 4, 1992 [WO] WIPO ............ PCT/US92/07448

[51] Int. Cl.$^6$ .................................. A61B 17/38
[52] U.S. Cl. .................... 606/24; 606/20; 606/26; 607/96; 607/105; 62/293
[58] Field of Search .................. 606/20–24, 26; 62/293; 607/96, 105

[56] References Cited

U.S. PATENT DOCUMENTS

| | | | |
|---|---|---|---|
| 3,333,587 | 8/1967 | Johnston | 606/23 |
| 3,369,550 | 2/1968 | Armao | 606/20 |
| 3,662,755 | 5/1972 | Rautenbach et al. | 606/24 |
| 3,907,339 | 9/1975 | Stumpf et al. | 606/20 |
| 4,211,086 | 7/1980 | Leonard et al. | 606/20 |
| 5,100,425 | 3/1992 | Fischell et al. | 606/159 |
| 5,334,181 | 8/1994 | Rubinsky et al. | |

FOREIGN PATENT DOCUMENTS

| | | | |
|---|---|---|---|
| 0808081 | 2/1981 | U.S.S.R. | 606/21 |
| 1153901 | 5/1985 | U.S.S.R. | 606/23 |
| 1303151 | 4/1987 | U.S.S.R. | 606/23 |

OTHER PUBLICATIONS

Cryostatic Congelation: A System for Producing a Limited, Controlled Region of Cooling or Freezing of Biologic Tissues, Irving S. Cooper and Arnold J. Lee, pp. 259–263.
Cryogenic Surgery of the Basal Ganglia, Irving S. Cooper, Aug. 18, 1962, pp. 600–604.

Primary Examiner—Stephen C. Pellegrino
Assistant Examiner—Jeffrey A. Schmidt
Attorney, Agent, or Firm—Sherman and Shalloway

[57] ABSTRACT

A closed end surgical cryoprobe instrument may have a probe shaft diameter of 3 millimeters or less and can achieve and maintain freezing zone temperatures close to that of the liquid cryogenic refrigerant. Using sub-cooled liquid nitrogen at approximately −208° C. freezing zone temperatures as low as −206° C. can be achieved in under 1 minute. The liquid nitrogen supply tube is provided with a plurality of small vent holes to vent gas formed or present in the refrigerant supply tube to the return refrigerant flow channel. The vent holes also allow small amount of liquid nitrogen to vent into the return flow channel to further reduce the temperature differential between the sub-cooled liquid nitrogen supply and the counter current flowing return refrigerant. Heat transfer is maintained through nucleate boiling. In place of vent holes, narrow slits may be provided in the supply tube. Alternatively, a sintered porous metal supply tube can be used as the vent means.

22 Claims, 8 Drawing Sheets

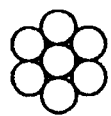 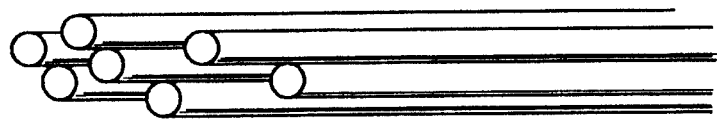
FIGURE 8A  FIGURE 8B
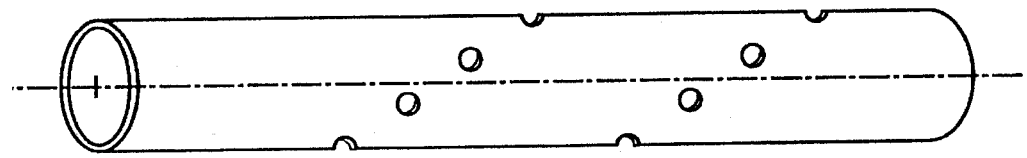
FIGURE 3

CRYOSURGICAL INSTRUMENT WITH VENT MEANS AND METHOD USING SAME

This is a continuation of application Ser. No. 08/137,353, filed Oct. 18, 1993, which in turn is a continuation in part of prior application Ser. No. 07/756,287, filed Sep. 6, 1991, now U.S. Pat. No. 5,254,116, and is also a continuation in part of PCT/US92/07448, filed Sep. 4, 1992.

1. Field of the Invention

This invention relates to a cryosurgical instrument suitable for use in destroying living tissues, such as solid malignant or benign tumors. More particularly, the invention relates to a surgical cryoprobe instrument capable of rapidly producing very low temperatures and maintaining very low temperatures even under heat conditions, such as, when surrounded by tissue, and which is highly effective in the surgical treatment of various disorders, specially in destroying tumors. Even more specifically, the invention relates to surgical cryoprobe with means for quickly producing at the probe tip temperatures below the melting temperature of tissue (−0.57° C.) and maintaining very low temperatures, using liquid cryogen, such as liquid nitrogen, as the coolant, which coolant temperatures can be lower than the normal boiling temperature of the liquid cryogen. The invention specifically relates to such cryoprobe instruments which have ventilation means, e.g., hole(s) in the liquid cryogen delivery tube, strategically positioned to vent gas formed in the liquid cryogen delivery tube into the exhaust tube before the gas reaches the tip of the cryoprobe and at a temperature which is lower than the temperature of the cryogen flowing in the exhaust tube.

2. Discussion of the Prior Art

Cryosurgical probes are used in a wide variety of surgical procedures including removal of cataracts, repairing detached retinas, treating cervicitis, cervical erosion, removal of cysts, etc. Until very recently, cryosurgery has been applied primarily to the outer surface of the body. However recent advances in cryosurgery have enabled its application to the removal of unwanted tissue deep in the body. These advances include the coupling of imaging techniques, such as ultrasound or magnetic resonance imaging with cryosurgery so that the extent of the tumors, as well as that of the frozen tissue can be readily ascertained. Moreover, Rubinsky and Pegg, Proc. R. Soc. Lond. B324, 343–358 (1988) have shown that the process of freezing in tissue and the ultimate destruction of frozen tissue is preceded by destruction of the vasculature network surrounding the tissue. It thus appears that the destruction of the frozen tissue is promoted by the lack of blood supply to the frozen tissue after thawing. Consequently, the thawed tissue is destroyed by ischemic necrosis. These authors also showed that tissue at the outer edges of the frozen region is most readily destroyed.

Most conventional cryoprobe instruments operate with liquid nitrogen ($LN_2$) or other liquified gas as the cooling medium. The $LN_2$ is introduced into the freezing zone of the probe through a feed or delivery tube, which is usually the innermost tube of three concentric tubes. The delivery tube extends into an expansion chamber at the closed probe tip end but terminates a distance from the tip. The $LN_2$ rapidly vaporizes and expands several hundred-fold (e.g., 600–700×) in volume at atmospheric pressure. As the liquid vaporizes, it absorbs heat from the probe tip to lower its temperature, theoretically to the normal boiling point of $LN_2$ (about −196° C. at 1 atm). When the cryoprobe is placed in contact with the tumor tissue, however, a nitrogen gas pocket inevitably forms close to the inner surface of the tip, which retards the liquid flow and consequently decreases the heat transfer efficiency. The returning nitrogen gas further warms the liquid nitrogen in the supply tube, making it more difficult to achieve low temperature in the probe tip. To avoid this cascading blockage and maintain a steady flow of $LN_2$ to the tip, conventional cryoprobes must be rapidly vented, which requires a large returning space and therefore a large overall diameter of the probe.

In addition, at start up of the surgical procedure with the cryoprobe tip placed in or on the diseased tissue, the heat load on the probe is especially high and long time periods are required to cool the probe tip to its lowest operating temperature. In practice, with conventional cryoprobes and using liquid nitrogen as the cryogenic refrigerant, the lowest tip temperatures are rarely below −160° C.

However, lower temperatures can provide higher efficiency in tissue destruction by freezing faster and by freezing larger areas with the same probe tip size or surface area. It is desirable to keep the diameter of the probe tip as small as possible to afford accuracy and control to the user, but this is complicated by the need to have a free flow of $LN_2$.

Because of the use of vaporization of $LN_2$ at the probe tip end to achieve cooling, liquid nitrogen has previously been considered to be suitable only for large cryoprobes, e.g. cryoprobes having probe tips having an outer diameter larger than about 4 mm. For miniature cryoprobes cold nitrogen or helium gas is often used instead of liquid nitrogen. This compromise has proven unsatisfactory because the heat transfer efficiency between the gas and the probe tip in contact with the tissue is very low and consequently, the ice ball created at the tip is not large enough and the temperature is not low enough for typical clinical applications. Moreover, the pressure used for such probes is often in excess of 500 or 600 psi, which requires special safeguards to prevent potential hazards.

Vaporization of $LN_2$ within the supply tube leading to the probe tip has previously caused considerable problems for large, as well as smaller cryoprobes. Vaporization of $LN_2$ within the supply tube is probably due to warming of the liquid nitrogen by the surrounding exhaust nitrogen gas returning from the tip. That is, because the exhaust gas is warmer than the $LN_2$ in the supply tube, there is counter-current heat exchange and the temperature of $LN_2$ in the supply tube is increased, resulting in further gas formation in the supply $LN_2$. This warming of the liquid nitrogen within the supply tube causes $LN_2$ to vaporize, forming nitrogen gas bubbles which impede the flow of $LN_2$ to the tip.

To some extent, these problems were solved in the cryosurgical probe and system disclosed in the commonly assigned, co-pending U.S. patent application Ser. No. 07/588,329, filed Sep. 26, 1990, in the name of B. Rubinsky, et al. Among other advantageous features disclosed in this prior application, the cryosurgical probe was designed to use sub-cooled liquid nitrogen for cooling the probe tip in the freezing zone, thereby enabling to achieve tip temperatures as low as −196° C. or below, without requiring evaporative cooling in the "expansion" chamber of the closed probe tip end. Consequently, the return nitrogen cryogen in the exhaust tube is maintained at a lower temperature than in conventional cryoprobes operating on the evaporative cooling principle. However, in practice, long initial start-up times were required to achieve the very low operating temperature at the tip. For example, even with high flow rates of the sub-cooled $LN_2$ it would take as long as 20 minutes or more for the probe tip temperature to reach minimum operating temperature, which was usually higher than −196° C. These long start-up periods, needless to say, could be quite inconvenient during surgery.

The present inventors have now discovered a solution to this problem which remarkably reduces the time required to lower the probe tip temperature in the freezing zone to as low as or below −196° C. (when using $LN_2$ at atmospheric pressure) to as little as 20 seconds or less. Furthermore, this result can be achieved with probe tips having diameters of as small as 3 millimeters or less, a result not previously achieved with conventional cryoprobes.

Accordingly, an object of this invention is to provide a cryosurgical probe device which can achieve high heat transfer efficiency in a miniature probe by directing liquid cryogenic refrigerant (coolant) to the probe tip under conditions which reduce vaporization of the refrigerant at the probe tip and in the refrigerant return line.

Still another object of this invention is to provide a cryosurgical probe device wherein the extent of counter-current heat exchange in the cryogen supply tube is decreased by venting a small volume (e.g. drops) of liquid nitrogen through holes provided along the supply tube.

A related and more specific object is to provide a cryosurgical probe instrument which allows small volumes (e.g. drops) of liquid cryogen to pass through vent holes in the cryogen supply tube and vaporize in the cryogen return tube resulting in a liquid to gas phase transition in the return tube which causes Joule-Thomson cooling of the liquid cryogen flowing through the cryogen supply tube.

Still yet another object of the invention is to provide a small, lightweight, and relatively inexpensive cryoprobe which can achieve greater and more efficient freezing for any given probe tip diameter than in presently available cryoprobes.

A further and principle object of this invention is to provide a cryosurgical probe device which requires a shortened period of time to cool the probe tip to the desired low temperature.

Yet another object of the invention is to provide a cryosurgical probe device capable of achieving and maintaining temperatures below −196° C.

It is still a further object of the present invention to provide a cryosurgical probe device which can produce a larger ice ball than with a conventional cryosurgical probe of similar diameter and under similar operating conditions.

Another and related object is to provide a cryosurgical probe instrument and system in which all components required for effectively performing a cryosurgical procedure are contained within a compact movable unit.

Still yet another object of the invention is to provide a cryosurgical system capable of operating at low pressure.

SUMMARY OF THE INVENTION

The above and other objects of the invention which will become more apparent from the following detailed description and accompanying drawings are, in part, provided by a cryosurgical instrument having a hollow probe tip having a closed end forming a freezing zone for freezing live tissue, the instrument including a first inlet for receiving cryogenic liquid refrigerant and a first outlet for removing cryogenic refrigerant, a refrigerant supply conduit for transporting cryogenic liquid refrigerant from the first inlet to the probe tip, an exhaust flow passageway for transporting refrigerant from the freezing zone to the first outlet, wherein the supply conduit and exhaust flow passageway are arranged as concentric inner and outer passageways, with the supply conduit forming the inner passageway and extending beyond the outer passageway in the freezing zone, the supply conduit including means for venting gas present in the supply conduit into the exhaust flow passageway while preventing free flow of liquid refrigerant from the supply conduit, and a thermal insulation chamber surrounding the concentric supply conduit and exhaust passageway and extending to the freezing zone. The venting means allows gas formed or present in the supply conduit to vent into the exhaust passageway so as to maintain a high flow rate of refrigerant through the supply conduit. The vent means also functions to decrease the extent of counter-current heat exchange between the supply $LN_2$ and return coolant by allowing liquid refrigerant to vent into the exhaust flow passageway and thereby reduce the temperature differential between the supply conduit and its surrounding exhaust passageway. As a consequence of the lowered temperature of the refrigerant in the exhaust passageway, vapors formed in the exhaust passageway are condensed or at least partially condensed and reduced in size to further prevent vapor blockage of the exhaust flow. Still further, in accordance with the preferred mode of operation of the cryosurgical probe, the degree of cooling of the refrigerant at the closed probe tip end and freezing zone and in the exhaust passageway is such that substantially only nucleate boiling of the liquid refrigerant occurs at the inner wall of the probe tip. Therefore, substantially all heat transfer between the object (e.g., tissue, tumor, etc.) being cooled (frozen) and the liquid cryogenic refrigerant is via nucleate boiling rather than film boiling or convection heat transfer.

In one embodiment of the construction of the inventive cryosurgical probe device, especially for the smaller diameter probes, such as below 6 millimeters, most especially below 4 millimeters, spacer means may be provided extending along the inner wall of the probe tip from the insulation chamber to a point beyond the downstream-most extent of the ventilation means. The spacer means reduces the surface area of the probe tip subject to heat transfer to the cryogenic liquid, thus reducing the amount of boiling which takes place to further increase overall efficiency, as measured, for example, by the size, shape and rate of formation of an ice ball in the object being cooled.

Preferably, the exhaust passageway is enlarged at the proximal end of the probe (corresponding to the handle portion, upstream from the freezing zone at the closed probe tip end) to promote unimpeded flow of the exhaust refrigerant. The supply conduit will preferably have an upstream-most extent of the vent means located in a region of the supply conduit surrounded by this enlarged area of the exhaust passageway with additional vent means extending towards the outlet end of the supply conduit in the vicinity of the closed probe tip end. The vent means of the supply conduit preferably includes a plurality of ventilation openings located longitudinally and downstream from a first ventilation opening in the enlarged area, and which downstream openings may be, and preferably are, of smaller diameter than the first ventilation hole, the most downstream ventilation opening most preferably being located spaced from the outlet end of the supply conduct and within the region surrounded by the thermal insulation chamber.

In a preferred embodiment, the supply conduit is in the form of a tube which has a downstream region (including at least the freezing zone) and upstream region (corresponding to at least the handle portion) relative to the distal or closed end of the probe tip, the upstream region having a larger diameter than the downstream region, thereby further promoting the rapid and unimpeded flow of the supply coolant to the freezing zone and allowing a smaller outside diameter in the region of the probe (e.g. probe shaft and tip) actually required for surgery.

In yet another embodiment, the exhaust flow passageway similarly has an upstream region (including at least the freezing zone, and preferably the probe shaft), a first downstream region generally located in the probe handle and having a larger diameter than the upstream region, and a second downstream region at the exhaust outlet which forms an enlarged chamber having an outer diameter larger than that of the first downstream region. The upstream area of the exhaust flow passageway in the probe shaft may include means to prevent contact between the wall of the exhaust tube and the outer probe shell whereby the formation of ice crystals in the upstream region area is inhibited.

In the preferred embodiment, the thermal insulation chamber is a closed vacuum chamber which may have a plurality of gas absorbing or adsorbing particles which may be adhered to the inner surface thereof, to further reduce the number of gas molecules and maintain a high vacuum.

BRIEF DESCRIPTION OF THE DRAWINGS

FIGS. 3 and 6 are side elevation views of alternative embodiments of vented supply tubes according to the invention.

FIGS. 8a and 8b are end and partial side elevation views, respectively, of still another embodiment of a vented supply tube according to the invention.

DETAILED DESCRIPTION OF THE INVENTION

Figure 1:
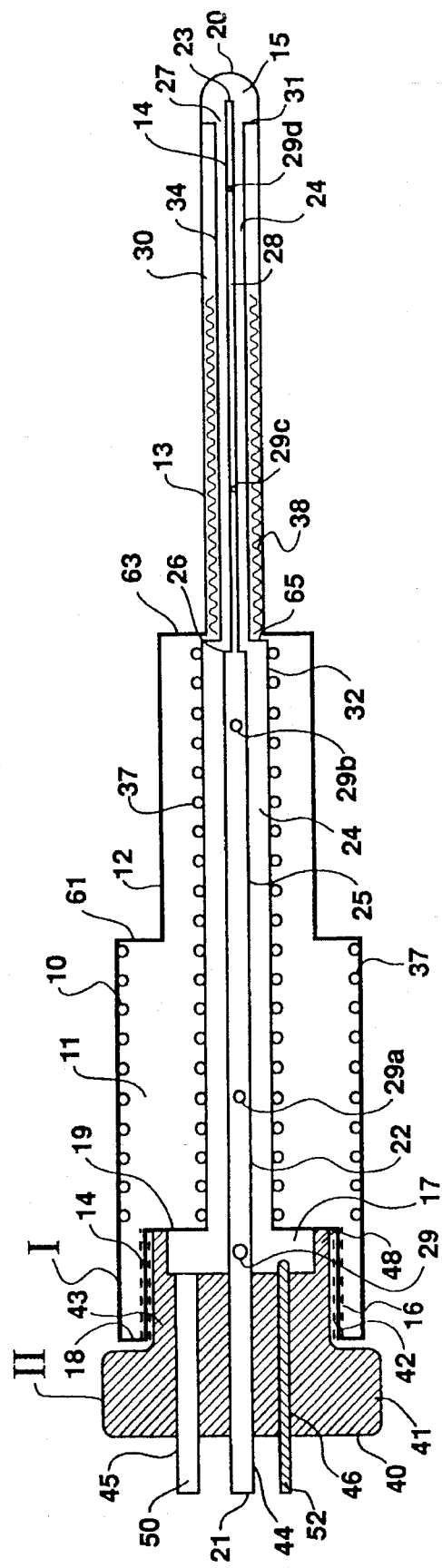
FIG. 1 is a sectional side view of one embodiment of the present invention.

The cryosurgical instrument of the present invention is a relatively small diameter cryosurgical probe of the type used to treat living tissue such as solid benign or malignant tumors. The cryosurgical instrument or cryoprobe may be of the same general construction and incorporate any or all of the features disclosed in the aforementioned Rubinsky, et al. U.S. patent application Ser. No. 07/588,329, the disclosure of which is incorporated herein by reference thereto. The cryosurgical instrument is cooled by a liquid refrigerant, such as, liquid nitrogen, however, other liquid refrigerants capable of generating subfreezing temperatures, especially below −60° C., can also be used to cool the probe. Examples of such cryogenic liquids include, for example, freon 14, freon 22, freon 13, liquefied air and normally gaseous hydrocarbons.

The following description will refer to liquid nitrogen ($LN_2$) as the cryogenic refrigerant, however, it is understood that similar considerations and advantages will be achieved using other cryogenic liquids with lower or higher boiling temperatures. Therefore, depending on the extent and rate of freezing required by the surgeon, $LN_2$ or other cryogenic refrigerant may be used with the inventive cryosurgical probe.

To achieve the full advantages of the surgical cryoprobe of the present invention, the liquid nitrogen refrigerant will be sub-cooled to a temperature below its normal boiling point (−195.8° C., 1 atm.) and generally above its normal freezing point (−210° C.). In general, the sub-cooled refrigerant will be cooled to a temperature ranging from about −198° C. to −210° C., preferably, from about −200° C. to −208° C., especially about −208° C., in the refrigeration system in which sub-cooling occurs. Therefore, by maintaining appropriate flow rates and sufficient thermal insulation, the sub-cooled liquid nitrogen can be delivered to the closed end of the probe tip at operating temperatures below the normal boiling point of liquid nitrogen, ($LN_2$), below −196° C., and especially about −206° C. Furthermore, using the invention cryoprobe to deliver sub-cooled $LN_2$, it becomes possible to lower the temperature of the cryogenic probe tip to at least −196° C. and especially −206° C., within a very short period of time, preferably within one minute and especially within 30 seconds after initiation of the delivery of sub-cooled $LN_2$ from the refrigeration system. The $LN_2$ may be supplied under relatively low pressure, such as 20 to 100 psi, preferably 40 to 90 psi, for example 60 to 80 psi. Good results have been obtained, for example, at 70 psi.

Although it is preferred to use sub-cooled $LN_2$ or other liquid cryogen at temperatures below the normal boiling temperature (i.e., at atmospheric pressure) it is understood that at higher pressures the boiling point is elevated and, therefore, sub-cooled cryogen at such elevated pressures may have temperatures which are higher than the normal boiling temperature but still be maintained in the liquid state. Sub-cooled cryogen at these higher temperatures may also be used in and with the cryosurgical probe of this invention.

One system for generating sub-cooled cryogenic refrigerant which may be conveniently housed in a mobile manifold unit or in a mobile cart storage and supply unit, is described in the aforementioned application Ser. No. 07/588,329, the disclosure of which is incorporated in its entirety herein by reference thereto.

The mobile cart may include one or more storage vessels for liquid nitrogen to be used as the cryogenic liquid refrigerant for the cryoprobe and also for use as the refrigerant for the refrigeration system.

According to a preferred embodiment of this invention such storage vessels, e.g. Dewars, may be arranged vertically relative to one another and connected through a series of valves in a manner so as to allow one dewar to act as an $LN_2$ retrieval vessel for collecting any $LN_2$ recovered from the cryoprobe during a surgical procedure. The vertical arrangement is another advantage of the present invention in that it eliminates the need to use high pressure to transfer $LN_2$ from a retrieval tank to a supply tank as in the aforementioned application. Instead, in the present arrangement, gravity flow can be used to facilitate the transfer of recovered $LN_2$ to the $LN_2$ supply tank from the retrieval tank. Such an arrangement allows for use of lower pressure to transfer $LN_2$.

At least one of the vertically arranged dewars and, preferably the upper dewar, may contain a slush chamber therein for sub-cooling the liquid cryogen to a temperature below its normal boiling point, for example at or near the triple point at which temperature liquid and solid nitrogen are in equilibrium and form a thickened mixture known as "nitrogen slush" in which liquid and solid nitrogen coexist. An upper $LN_2$ supply dewar, for example, may contain a slush chamber. The lower dewar can then function as a pressurized dewar to drive the system. The lower dewar is initially filled with $LN_2$ from a large supply tank or from an existing $LN_2$ supply line which may be available in a hospital or surgery room. To facilitate filling of the lower pressurized dewar to the operating pressure, e.g., 60–80 psi, it is convenient, as is known in the art, to provide a diffuser at the inlet to the vessel, the diffuser preventing or minimizing $LN_2$ jet formation which could otherwise expel $LN_2$. Such an arrangement provides a more compact system for sub-cooling liquid cryogen for use with the cryoprobe instrument. Other refrigeration units for sub-cooling the liquid cryogen, especially liquid nitrogen, are known in the art and can be used in this invention, for example, U.S. Pat. Nos. 3,455,117, 4,620,962, 4,296,610, 4,715,187 and 4,716,738, the disclosures of which are incorporated herein by reference thereto. In any case, whichever refrigeration system is used, one of the prominent advantages of the cryoprobe of this invention is that due to its more efficient utilization of the cryogenic refrigerant, and the very substantially reduced time required to achieve operating temperatures, the volume of the $LN_2$ storage dewar(s) can be substantially reduced for any given operation, thereby making the overall system more compact and less expensive.

An important advantage of the very low probe tip temperatures made possible by the use of sub-cooled $LN_2$ as the probe refrigerant is the ability to reduce the diameter of the probe tip while maintaining high freezing capacity. For example, according to the present invention, a probe tip outer diameter as small as about 1.5 to 3 millimeters can be used effectively for freezing much larger areas of tissue than for conventional cryoprobes of the same or larger diameter. Of course, larger probe tips can also be used, for example, up to about 10 millimeters. In general, however, for practical reasons, the minimum probe tip outer diameter is about 2.5 mm, and for most purposes is 3 mm. Probe tip diameters greater than about 10 mm are not generally required to achieve the required degree and extent of freezing, even for large size tumors and, therefore, will not usually be used.

Moreover, another important and distinct advantage of the cryoprobe instrument of this invention is that due to its highly effective use of small probe tip diameters, e.g., 3 mm, the surgeon may use multiple probes, e.g., 3, 4 or 5, strategically located in the defective organ or tumor to maximize efficiency in freezing the entire organ or tumor.

The cryoprobe instrument of the present invention includes a body or handle portion and a probe shaft which is the operative portion and includes the freezing zone and closed end probe tip which come into contact with the tissue to be treated. Each of the body portion and probe shaft have an outer shell or casing formed from hollow tubing (all tubing used in the cryoprobe is generally and preferably of cylindrical cross-section). The outer shell may be a single piece of constant diameter, as in the probe of the aforementioned Rubinsky, et al. application and other conventional cryoprobes, and similarly the refrigerant supply conduit and refrigerant exhaust passageway which extend through the body portion and probe shaft may be formed from concentric tubes of constant diameter throughout their length.

However, in accordance with the preferred embodiment of the cryoprobe instrument of this invention the outer casing for the probe shaft has a smaller diameter than the outer casing of the body portion. Similarly, the concentric cryogen supply tube and exhaust tube have larger diameters in the body portion than in the probe shaft. Accordingly, the larger diameter sections provide less impedance to the free flow of the liquid cryogen from the cryogen supply vessel and connecting tubing through the cryogen supply tube until the reduced diameter portion in the probe shaft, and similarly, less impedance to flow and opportunity for boiling of the refrigerant flowing from the closed probe tip end through the exhaust channel out of the cryoprobe instrument, either to be vented into the atmosphere, or preferably, returned (recycled) to a collection vessel. Even more preferably, the exhaust passageway includes an enlarged portion at the proximal or open end of the probe body/handle portion.

The sections of tubing of different diameter can be constructed of a single piece but more typically is formed from separate tubing sections welded together with fluid tight seals to appropriately dimensioned annular end pieces, e.g., washers, at the junctions of each tube section.

The space between the outer shell casing and the refrigerant exhaust tube is filled with thermal insulation to prevent the shell, except at the freezing zone at the distal end of the probe shaft, from attaining freezing temperature, as is well known in the art. The thermal insulation may be provided by air or other gas, or by solid thermal insulating material. The preferred thermal insulation, however, is a vacuum, which may be an active vacuum as in the Rubinsky, et al. application, but generally is a fixed, permanent vacuum. Furthermore, in accordance with a preferred embodiment a gas adsorbent, such as activated charcoal or zeolite, for example, may be included within the vacuum chamber to further lower the pressure by adsorbing any gases not evacuated from the chamber when the chamber is sealed, or any gas which may leak into the vacuum chamber. The adsorbent is used in the form of solid particles, such as pellets or granules, or, less preferably, a powder and is preferably adhered to the inner walls of the vacuum chamber using adhesive, e.g. epoxy, or by fusing or sintering. Having the adsorbent particles adhere to the walls is advantageous to avoid clumping, thereby maximizing available surface area available for adsorbing any residual gases. Using larger size particles or granules facilitates bonding the particles to the tubing walls with minimum interference of available gas adsorbing surface area. In practice, vacuums as low as about $10^{-7}$ mmHg have been formed. In the preferred embodiment, the larger and smaller diameter sections of the supply tube coincide with and are concentrically located within the similarly larger and smaller diameter sections of the exhaust flow tube as well as the larger and smaller diameter sections of the outer casing.

As may readily be appreciated, especially for the preferred cryoprobe instruments of very small probe shaft diameters, e.g. below about 6 mm, especially below 4 mm, such as 2.5 to 3 mm, there is only a very small clearance between the refrigerant supply tube outer wall and the exhaust tube inner wall and between the exhaust tube outer wall and the vacuum chamber wall or inner wall of the outer shell. Accordingly, it is within the scope of the invention to provide a protective insulating tape, such as Teflon tape, for example, wrapped around the exhaust flow tube so as prevent contact between the exhaust tube and outer shell. Such insulation serves to prevent the formation of ice crystals on the outside of the shell casing.

The open (proximal) end of the body portion of the cryoprobe instrument is connected to the refrigerant supply vessel and associated delivery tubing or conduits, and any necessary electrical supply lines, via a delivery connector, usually through appropriate coupling means, such as screw threads. Thus, the refrigerant $LN_2$ delivery connector may include at one end thereof a means for fluid tightly receiving one end of the external (to the cryoprobe instrument) $LN_2$ supply and return tubes and electrical wiring and at the opposite end means for fluid tightly receiving the open (proximal) end or base of the probe body, e.g. a male threaded portion which engages with female threads of the probe body.

Solid metal electrical contacts or male and female electrical connectors or thermocouple pins may also be provided on each of the mutually mating ends of the delivery connector and probe base such that when the parts are assembled the metal electrical contacts or male and female connectors are in electrical contact with each other to complete the electrical wiring circuit to a thermocouple at or near the probe tip. In a preferred embodiment, a thermocouple joint is formed at the end of the $LN_2$ supply tube and thermocouple wires run through the space between the $LN_2$ supply tube and the exhaust flow tube and connect to the thermocouple pins.

The delivery connector may be molded from Teflon or similar self-lubricating, low friction plastic or resin material with relatively low heat transfer coefficient.

When the probe body is connected to the $LN_2$ delivery connector the probe's internal $LN_2$ supply tube will extend into or through the delivery connector so that its inlet end may be connected in fluid flow communication with the $LN_2$ supply. The probe's exhaust flow tube may terminate at the open end of the probe's base and communicate with an enlarged chamber of the delivery connector such that exhausted refrigerant from the probe tip will flow through the exhaust flow tube and enlarged chamber and will be in fluid flow communication with a cylindrical bore extending through and located in the delivery connector spaced in axial alignment with the longitudinal axis of the probe. A second cylindrical bore extends through the delivery connector and is in axial alignment with the longitudinal axis of the probe. The second cylindrical bore has substantially the same diameter as the outside diameter of the $LN_2$ supply tube so that a fluid tight compression fit is formed between the periphery of the tube and the cylindrical bore.

The most prominent and distinguishing feature of the cryoprobe instrument of the present invention is an internal venting system which provides for the free flow of $LN_2$ through the supply tube and also maintains the exhaust refrigerant in the exhaust flow tube at a lower temperature than in conventional cryoprobes, thereby maintaining a lower temperature of $LN_2$ in the supply tube, ultimately resulting in lower temperatures, such as, for example, $-206°$ C. at the probe tip. Moreover, the internal venting system of the present invention allows the probe tip to achieve lower temperatures significantly faster than conventional cryoprobes including the improved probe of the Rubinsky, et al. application.

The internal venting system of the present invention is provided along the $LN_2$ supply tube. In one embodiment the $LN_2$ supply tube is provided with a series of small holes, which are sufficiently small as compared to the inside diameter of the $LN_2$ supply tube to prevent the free flow of $LN_2$ from the $LN_2$ supply line but large enough to allow any gas within the $LN_2$ supply line to escape through the holes into the surrounding exhaust flow tube as well as some liquid leakage into the exhaust tube. The vent holes provide three major functions in the cryoprobe instrument: 1) to maintain a high flow rate of $LN_2$ from the $LN_2$ inlet to the probe tip by venting any nitrogen or other gas present in or formed in the $LN_2$ supply tube before the gas can impede the free flow of $LN_2$ through the probe's $LN_2$ supply tube, 2) to vent gas along the supply tube which may be formed by counter-current heat exchange between the exhaust refrigerant and the colder supply $LN_2$ and 3) to decrease the extent of the counter-current heat exchange by venting some $LN_2$ drops through the holes into the returning path of the exhaust refrigerant including any gas bubbles formed by nucleate (or film) boiling, thereby cooling or reliquefying gas bubbles formed in the exhaust $LN_2$. This function, in particular, serves to maintain the boiling heat transfer phenomenon as nucleate boiling, rather than film boiling. As used herein, and in the appended claims, "nucleate boiling" refers to the type of heat transfer which occurs as discrete bubble formation at nucleation sites at the liquid solid interface and is associated with high rates of heat transfer per unit of area (heat flux). This is the type of boiling initially observed when boiling a pot of water. "Film bolling," on the other hand, is used to refer to the condition in which a vapor film forms on the solid surface and is characterized by low thermal conductivity and reduced heat flux. In addition, the large volume of bubble formation during film boiling tends to cause blockage of the exhaust tube.

A possible secondary effect of the vent holes is the additional cooling by Joules-Thompson phenomena which occurs when $LN_2$ in the supply tube is vented through the small vent holes into the exhaust flow tube. The resulting lower temperature of the exhaust refrigerant may thus serve to decrease the formation of gas in the supply tube.

While simple drilled holes along the length of the supply tube have been used with good results other forms of vent means may be used. For example, the vent means may take any form which permits gas formed in the supply tube to vent into the exhaust tube and may also allow small amounts of liquid to flow into the exhaust tube, but without interfering with the free flow of $LN_2$ through the supply tube.

It has not yet been confirmed whether the flow of liquid $LN_2$ from the supply tube to the exhaust tube through the vent holes is in the form of discrete droplets, or perhaps as a fine liquid stream. Moreover, the exact amount of supply $LN_2$ flowing through the vent holes into the exhaust tube has also not yet been ascertained. Nevertheless, it is believed that as much as fifty percent of the $LN_2$ entering the $LN_2$ supply tube may flow into the exhaust tube through the vent holes, depending on the number, size and location of the vent holes, and the operating pressures. Ideally, the cryoprobe will be designed and operated under conditions which uses the lowest total volume of $LN_2$ for any given operation, while minimizing the temperature differential between the $LN_2$ in the supply tube and in the exhaust tube and maintaining nucleate boiling and minimum (coldest) temperature at the freezing zone and closed end of the probe tip. The appropriate flow of $LN_2$ through the supply tube and vent holes to achieve the desired results can be determined through routine experimentation, as can the optimum location, number and size of the vent holes (or other vent openings). For instance, operating efficiency for any particular design may be determined on the basis of the size and shape of the ice ball formed when the cryoprobe is inserted in a vessel of water at a given temperature (e.g., room temperature or 98.6° C., etc.), as well as the amount of time required for ice ball formation and the amount (e.g., volume) of $LN_2$ used.

In addition to a series of vertical holes drilled along a straight line coinciding with the longitudinal axis of the probe, the holes may be drilled at an angle with respect to the longitudinal axis, or the openings may be punctured or provided with a cover or shroud, such as by being bent or displaced at the forward edge of the opening. Alternatively, in place of discrete holes or other apertures the supply tube may be provided with a thin slit or slits extending along a straight or spiralled line over a portion of the supply tube. As still another alternative to discrete apertures or slits, the supply tube may be formed of sintered metal particles providing a gas/liquid permeable porous structure over the entire length of the tube or over one or more portions of the tube.

The internal venting system of the present invention may include an enlarged chamber at the probe base in communication with the exhaust flow tube. This enlarged chamber facilitates the flow of the returning exhaust refrigerant. In a most preferred embodiment, a hole is provided in the supply tube in a region surrounded by the enlarged chamber of the probe base and delivery connector. This hole is generally larger than any downstream vent holes, for example, about 0.008 to 0.050 inches, preferably about 0.01 to 0.040 inches, e.g., 0.020, 0.025, 0.030, 0.035, or 0.038 inches, for a supply tube having an inner diameter in the range of from about 0.040 to 0.080 inches. The effect of this rearward-most hole is to shorten the time required to cool the probe tip ("cool-down" period) by rapidly venting any gas present in the, or formed in the, refrigerant delivery tube and $LN_2$ supply tube at the initiation of operation of the probe when the system has the highest heat load.

The cryogenic probe of the invention is also advantageously designed to have a larger diameter supply and exhaust flow tube in the downstream region of the instrument body relative to the probe tip than in the upstream region, i.e. the probe shaft. This widening of the exhaust flow and $LN_2$ supply tubes decreases flow resistance of $LN_2$ and any returning gases. Smaller diameter tubes are used in the distal portion of the instrument that is actually required for surgery, such as the probe tip and an upstream region from the probe tip constituting the remainder of the probe shaft.

The size of the downstream ventilation holes is also an important feature in the internal venting system. The diameter of the holes may vary depending on the outer diameter of the $LN_2$ supply tube as well as the location of the hole(s), but in all cases the vent holes are smaller than the inner diameter of the $LN_2$ supply tube. For example, the ventilation holes located along the supply tube may have an outer diameter of from about 1/10 to 8/10 the inner diameter of the supply tube at the probe tip end. According to a most preferred embodiment of the invention, the ventilation holes have a diameter in the range of from about 0.004 to about 0.020 inch, preferably 0.004 to 0.015 inch, especially preferably less than 0.010 inch.

The rearward-most ventilation hole of the supply tube surrounded by the enlarged chamber at the upstream end of the exhaust flow tube preferably has a larger diameter than that of the downstream ventilation holes located longitudinally along the supply tube, for example, about 1.5 to 2.5 times larger, such as twice as large in diameter.

The location of the ventilation holes relative to one another along the supply tube has an effect on the efficiency of gas ventilation and exhaust gas cooling. In a most preferred embodiment of the invention, the holes are spaced equidistant from one another, however, equidistant spacing is not essential. The holes may be formed in any region of the supply tube, i.e. in the narrowest diameter region located within the probe shaft, in the first downstream region of the supply tube having a larger diameter, and in the proximal downstream region of the supply tube, which is surrounded by the enlarged chamber of the delivery connector/exhaust flow tube. Preferably, in addition to the large hole communicating with the enlarged chamber one, two or more vent holes are included in each of the small diameter and large diameter sections of the $LN_2$ supply tube. In a preferred embodiment, a single hole having a diameter of about 15–28 mil (0.015 to 0.028 inch) is located in the proximal region of the supply tube and one or two to five or six smaller holes having diameters in the range of about 4 to about 14 mil, preferably from about 4 mil (0.004") to 10 mil (0.010"), are located in the narrowest diameter section and/or larger diameter section intermediate the proximal end and the narrowest diameter section. The number of venting holes may vary depending on their diameters, the operating pressure, cool-down period requirement, minimum temperature required by the surgeon, the length of the cryoprobe instrument, and the like, but generally from 2 to 15, preferably 2 to 12, most preferably 2 to 8, vent holes in total, will be sufficient. The forwardmost hole with respect to the outlet of the supply tube in the vicinity of the closed end of the probe tip is preferably located outside of the freezing zone, namely in the region of the supply tube surrounded by the thermal insulation chamber. For example, for a 3 mm O.D. probe shaft having a freezing zone length of about 0.5 inch, the forwardmost hole may be about one inch from the outlet end of the supply tube.

As shown in the Referential Example provided below an optimization study of the location, size, and number of vent holes demonstrated that the holes, particularly the big hole in the return chamber, primarily function to reduce the cool-down time by venting the gases generated in the $LN_2$ transport conduits during the cool-down period. The more holes, the faster the cool-down process. A hole of any size located in the $LN_2$ return chamber is approximately 45% more efficient in venting gases compared to the downstream holes of the same size along the supply tubing. In a condition of minimum working load such as a small tumor with lower surrounding temperature, a fast response attained by multiple venting holes in relatively large size along the supply tubing might be desirable. In this case, the liquid nitrogen will still be able to reach the probe tip. In a condition of maximum working load such as in a relatively large tumor with relatively high surrounding temperature, however, a large portion of liquid nitrogen will shunt from the probe tip due to the back pressure created by the gaseous nitrogen in the chamber at the probe tip. This extreme condition was observed for a vent hole pattern with 1 large rear hole and 7 smaller downstream holes.

To maintain a large portion of liquid flow to the probe tip chamber, the big vent hole in the return chamber might be eliminated and multiple smaller vent holes provided along the supply tube. The elimination of the big hole in the return chamber, however, will inevitably increase the time period to vent the gases generated in the $LN_2$ transport hose, even though the probe will still be able to ultimately "kick out" after a "waiting period." In an extreme case, the "waiting period" become indefinite when there is no vent hole. If cost to drill small holes is not a factor, the "waiting period" could be reduced to a level comparable to that attained by a big vent hole in the $LN_2$ return chamber. One major disadvantage of a big hole located in the return chamber is that is causes greater nitrogen consumption compared to multiple small holes in other locations along the supply tube. If all factors are taken into consideration such as the overall nitrogen consumption, the size of the ice ball, the cool-down period, and the manufacturing cost, one optimum pattern of supply tube vent holes appears to be a big vent hole in the return chamber in combination with multiple downstream "mini" holes. The size of the big hole can be conveniently selected depending on such factors as the acceptable pre-cooling time and surgical duration as given by the surgeons. The most optimum location, the number and size of the mini holes are more difficult to determine, but could be determined for particular working condition of the cryoprobe, such as the size of tumor and the temperature of its surroundings.

With regard to total nitrogen consumption as a function of hole pattern (size, number and position) it is noted that for two-phase flow (liquid-gas) the discharge rate to the probe tip increases uniformly as the supply pressure increases, at least in the lower supply pressure range. Gradually, a critical point will be reached where the mass flow of nitrogen escaping from the discharge end of the supply tube achieves a maximum, which then cannot be exceeded by further increasing the supply pressure.

The prediction of the critical point is complicated by the nature of cryogenic flow, largely because of the changes in vapor and liquid ratio (quantity) and the mass, heat and momentum exchanges taking place at the vapor-liquid interface. The critical point of mass flow, however, can be adequately estimated by an extended experiment in which a homogenous flow to the probe tip is maintained by sub-cooling the $LN_2$ and subsequently minimizing the heat loss along the $LN_2$ transport system.

Since the pressure decreases as nitrogen flows in the supply tube, the rate of nitrogen gas or liquid escaping from the hole will vary from hole to hole, depending upon the position of the hole on the supply tube. At maximum operating conditions, however, the mass flow m of $LN_2$ discharged to the probe tip will be a constant, regardless of the hole pattern. Here, the holes are assumed to function only to vent the gas and accelerate the process to attain the maximum flow conditions. Assuming the critical mass flow is $m_c$, then:

$$m_c = \frac{mA_e}{A_e + \sum_{i=1}^{n_b} \alpha_i A_{bi} + \sum_{j=1}^{n_s} \beta_j A_{sj}} \quad (1)$$

$$\frac{A_{bi}}{A_e} = k_{bi} \quad (2)$$

$$\frac{A_{sj}}{A_e} = k_{sj}. \quad (3)$$

$A_c$, $A_{bi}$, $A_{sj}$, denote the cross section areas of the discharge end, the big hole(s) and small hole(s), respectively, and $\alpha_i$ and $\beta_j$ denote the pressure drop factors for the big hole(s) and small hole(s), respectively.

Re-arranging equation 1, then:

$$\frac{m}{m_c} = 1 + \sum_{i=1}^{n_b} \alpha_i k_{bi} + \sum_{j=1}^{n_s} \beta_j k_{sj}.$$

The above equations are universal and applicable for all hole patterns and probe sizes.

For a 3 mm cryoprobe with a return chamber, the equations may be simplified as:

$$\frac{m}{m_c} = 1 + n_b \alpha_b k_b + n_s k_s.$$

Accordingly, the total nitrogen consumption for five probes in volume, V, over 15 minutes operating time period will be:

$$V = 17.35 (1 + n_s k_s), \text{ if } n_b = 0$$
$$22.65 (1 + n_b k_b + n_s k_s), \text{ if } n_b \geq 1.$$

If the small (mini) holes are 0.001" and the big hole 0.025" the above equation can be further reduced to:

$$V = 17.35 + 2.05 \, n_s, \text{ if } n_b = 0$$
$$22.65 + 11.55 \, n_b + 2.67 \, n_s, \text{ if } n_b \geq 1$$

where $n_s$ and $n_b$ denote the total numbers of small and big holes, respectively.

It is also possible for the ventilation means to extend into the freezing zone, (i.e., probe tip chamber), namely beyond the forwardmost end of the insulation chamber. For example, where the supply tube is formed entirely from porous sintered metal the pores will naturally extend beyond the thermal insulation chamber into the freeze zone. In the case of ventilation hole(s) extending into the freezing zone, however, it is often preferred to provide a spacer, which may be, for example, a solid annular disc, positioned abutting at its one (upstream) end against the forwardmost end of the insulation chamber, and extending at its other (downstream) end towards the closed end of the probe tip, a distance extending beyond the forwardmost ventilation hole, but terminating at, or just slightly before, i.e., upstream of, the outlet end of the $LN_2$ supply tube. The outside diameter of the spacer disc will be the same as the inside diameter of the probe casing in the probe shaft so as to form a fluid tight fit. The diameter of the annular opening of the spacer should be less than the diameter of the inlet opening of the exhaust flow tube (e.g., the inside diameter of the insulation chamber) so as not to impede or obstruct flow of the refrigerant into the exhaust flow tube. The spacer is especially useful in the smaller diameter probes, e.g., 4 mm or smaller, especially 3 mm or smaller, and apparently functions by reducing the available surface area for heat transfer. The spacer may be made from a poorly heat conductive material, in which case the length of the freezing zone is effectively reduced, or it may be made from a moderate to high heat conductive material which will still permit cooling of the probe shaft in the freezing zone, while still reducing the degree of boiling of the liquid refrigerant.

An example of a cryosurgical instrument according to the invention is illustrated in FIG. 1. It is understood that the invention is not intended to be limited to the exact embodiments of the example, as many variations of the invention can be made.

Referring to FIG. 1, an embodiment of the cryoprobe instrument will be described. The cryoprobe instrument is shown generally at I and the $LN_2$ delivery connector is shown generally at II.

Figure 2:
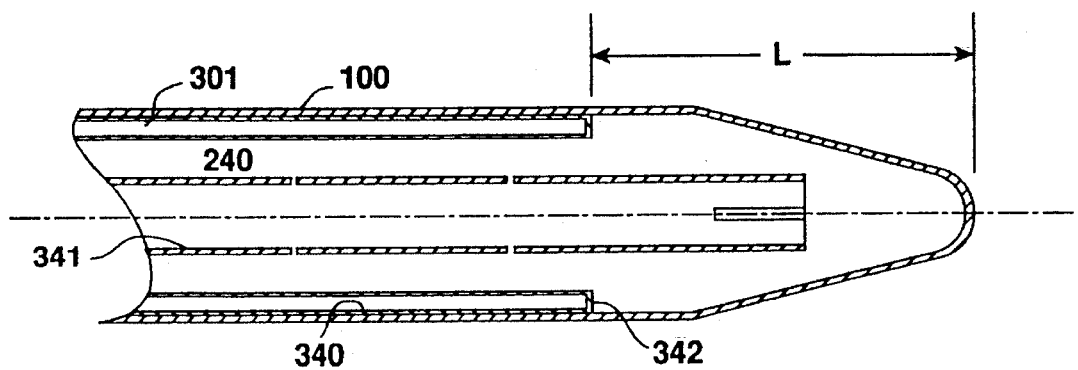
FIG. 2 is a sectional side view of an alternative embodiment of a portion of the cryosurgical probe tip including a movable vacuum chamber and adjustable freezing zone.

The outer shell or casing of the probe is shown generally at 10 and includes a large diameter upstream body portion 11, fluid tightly connected, e.g., by welding, via stainless steel washer 61 to intermediate portion 12, which, in turn, is fluid tightly welded via stainless steel washer 63 to probe shaft 13. Probe shaft 13 includes a closed end or tip 20 which includes the freeze zone 15 located downstream (distally) of vacuum insulation chamber 30. In the embodiment shown in FIG. 1 the freezing zone is of fixed predetermined length with end wall 31 of vacuum chamber 30 being welded tightly to the inner wall of probe shaft 13. End wall 31 may be formed as a flange or flare at the end tube 34, or may be a separate stainless steel washer. However, as shown in FIG. 2, it is also within the scope of the invention to provide a movable vacuum chamber 301 to adjust the length L of the freeze zone. For example, whereas in the embodiment of FIG. 1 only three concentric tubes are used to provide the vacuum chamber, $LN_2$ supply tube and refrigerant exhaust channel, it is possible to provide a fourth concentric tube 340 in sliding contact with the outer casing 100, which, together with the intermediate concentric tube 341 forming the outer wall of the refrigerant exhaust channel 240 to which the end 342 of the fourth tube is tightly welded, forms the thermal vacuum insulation chamber 301. Then, by moving the casing 100 relative to the end of the vacuum chamber, and forming a fluid tight seal between the casing and the vacuum chamber, the length L of the freezing zone may be increased or decreased, depending on, for example, the size and depth of the solid tumor being treated. The fluid tight seal may be formed, for example, by crimping the casing near the end of the vacuum chamber, or by an appropriate, low temperature sealant provided between the outer casing and the "contacting" wall of the vacuum chamber.

Whether, the cryoprobe is constructed with a fixed length freeze zone as in FIG. 1 or an adjustable length freeze zone as in FIG. 2, the cryoprobes can be designed to provide a wide range of freeze zone lengths, for example, from about ½ to 1 centimeters (or about ¼ to ½ inch) to about 6 or 7 centimeters (about 2 to 3 inches), although in some special cases, shorter or longer freeze zones may be useful.

The $LN_2$ supply tube 22 providing $LN_2$ supply passageway includes large diameter upstream section 25 and reduced diameter section 28 welded together via washer 26 which is shown located near the downstream end of intermediate body section 12. The reduced diameter section 28 extends through most of probe shaft 13 extending beyond the end 31 of the vacuum chamber which is coextensive with the inlet 27 of the exhaust refrigerant flow channel or passageway. The outlet end 23 of supply tube section 28 may be slotted (as shown in FIG. 2) to facilitate flow of the $LN_2$ to the closed end of the probe tip and freezing zone.

The exhaust flow passageway or channel 24 for removing used $LN_2$ from the freeze zone is defined, on the one hand, by the outer surface of supply tube sections 28 and 25, and on the other, by the inner surface of the smaller diameter exhaust flow tube 34 and larger diameter exhaust flow tube section 32 and continuing into the enlarged hollow chamber 17 at the open (proximal) end of the probe. Tubes 32 and 34 are concentric with $LN_2$ supply tube sections 25 and 28 and together with inner surface of probe casing tubing 11, 12 and 13 and end wall 18, wall section 14, and rear wall 19 (defining chamber 17) define the vacuum insulation chamber 30. End walls 18 and 19 may also each be comprised of stainless steel washers while wall section 14 may be a threaded bushing designed to sealingly mate with threaded $LN_2$ delivery connector II. Solid adsorbent particles 37, such as zeolite powder, are adhered to the inner surface of the walls of the vacuum chamber in the body portion 11 and intermediate portion 12 to help reduce the amount of gas in the vacuum chamber. Also, Teflon insulation tape 38 is shown wrapped around the outer surface of exhaust flow tube section 34. Tape 38 serves to prevent point contact between tube section 34 and concentric probe shaft 13 and therefore inhibits formation of ice crystals on the outer surface of the probe shaft during use. Although shown only at the proximal or upstream end of tube 34, protective insulative tape 38 may be provided over substantially the entire length of tube 34.

$LN_2$ supply tube 22 is shown with 5 vent holes, including rearwardmost vent hole 29, intermediate section vent holes 29a, 29b and forward vent holes 29c and 29d. Vent hole 29 is formed with a larger diameter than vent holes 29a–d and when supply tube 22 is fully inserted into the probe as shown in FIG. 1 vent hole 29 is located in enlarged chamber 17. More or fewer vent holes and different locations of the vent holes may also be used. For example, while all of the vent holes are shown as formed in a straight line coinciding with the longitudinal axis of the probe, the holes may be staggered or spiraled around the circumference of the supply tube sections such as shown in FIG. 3. Generally, and preferably the holes extend through only one wall around the circumference, however, the holes may also be drilled through both circumferential walls, e.g., spaced 180°.

Figure 4:
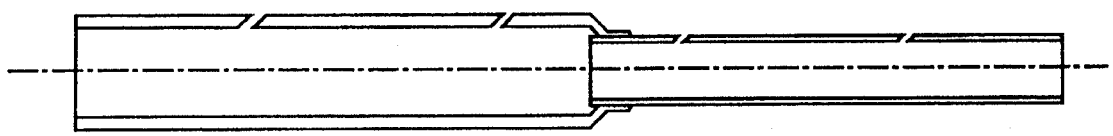
FIGS. 4, 5 and 7 are sectional side elevation views of other alternative embodiments of the vented supply tubes according to the invention.
Figure 5:
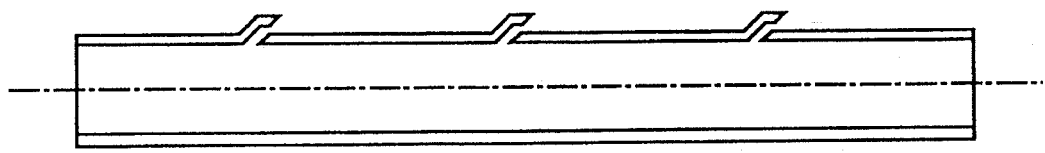
Figure 6:
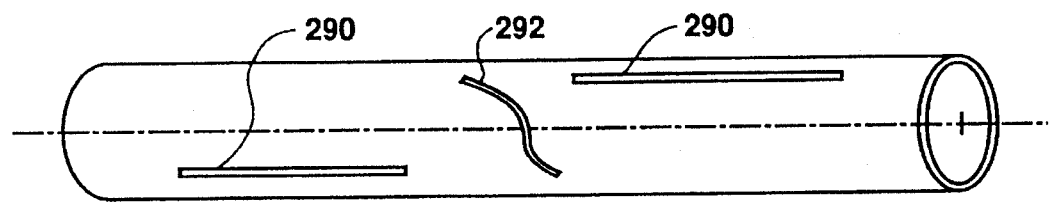

Rather than straight-through holes, as in FIGS. 1, 2 and 3, the holes may be angled as shown in FIG. 4. Preferably, the angle formed by the axis of the holes with respect to the longitudinal axis of the supply tube is from 20° to 80°, preferably 30° to 70° It is also within the scope of the invention to provide covered or forward shrouded openings which may be straight-through holes, or as shown in FIGS. 5a and 5b are preferably angled, as in FIG. 4. FIG. 6 shows an embodiment of the invention in which rather than discrete holes or apertures, thin slotted openings provide the ventilation means. These slotted openings may be straight, as shown at 290, or spiralled, as shown at 292.

Figure 7:
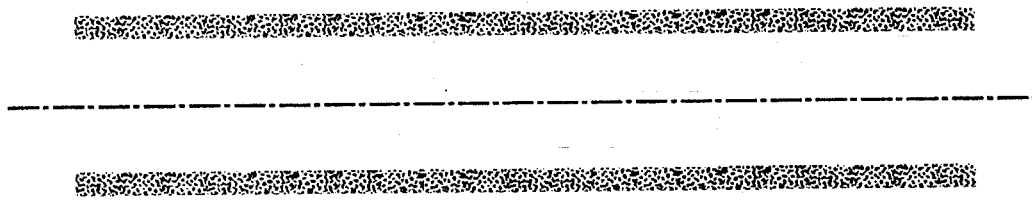

According to still another embodiment the ventilation openings may be formed as pores in a sintered metal tube, such as schematically illustrated in FIG. 7.

In the embodiment shown in FIGS. 8a and 8b vented supply tube is formed from a plurality of individual supply tubes of different lengths bundled together such that the outlet end of each tube is staggered along the longitudinal length of the probe.

In practice, the probe may be assembled by providing probe shaft 13 as an open ended tube to provide access to the end 31 of exhaust flow tube section 34 which end 31 is welded to the inner surface of the probe shaft after vacuum chamber 30 is evacuated. Alternatively, vacuum chamber 30 may be evacuated through end wall 18 or at any intermediate location using techniques well known in the art. For example, in the embodiment illustrated in FIG. 9, copper tubing 60 is provided near the rear end of wall 11 in flow communication with vacuum chamber 30 through aperture 66. Tube 60 provides an evacuation port for evacuating chamber 30, and after evacuation to the desired low pressure, tube 30 is sealed tightly using either a plug or by pinching the tube upon itself, or both, or any other suitable technique. Tube 30 may, alternatively be located at end wall 80, similarly to the tube 88. Before chamber 30 is evacuated exhaust tube end 31 is fluid tightly welded to probe shaft tube 13 and the closed tip end 20 is welded to the probe shaft tube 13 and the weld is appropriately polished to provide a smooth outer surface. It should be noted that in the previously described alternative embodiment illustrated in FIG. 2, utilizing four concentric tubes, with the vacuum chamber in sliding contact with the probe shaft tube, the end of the vacuum chamber will not be welded to the inner surface of the probe shaft as in the embodiment illustrated in FIGS. 1 and 9.

Referring again to FIG. 1, the liquid nitrogen delivery connector II is shown as a cylindrical body 40 formed from low friction, low temperature insulative, low expansion coefficient material, such as Teflon. The enlarged diameter section 41 may have a slightly larger diameter than that of body section 11. Reduced diameter section 43 includes male threads 42 which threadingly and sealingly engage with female threads 16 on wall section 14. Additional sealing means such as an O-ring (not shown) may also be provided to ensure a fluid tight seal between the connector and probe.

Connector 40 is provided with generally cylindrical through bores. Bore 44 is located on the longitudinal axis of the probe and is of substantially the same or slightly smaller diameter than the outer diameter of $LN_2$ supply tube section 25 to fluid tightly receive the $LN_2$ supply tube section 25. As shown in FIG. 1, the inlet end 21 of $LN_2$ supply tube 22 extends beyond the delivery connector for attachment to an $LN_2$ delivery line (not shown) and the outlet end 23 extends into freeze zone 15 spaced from but in close proximity to the closed tip end 20. Connector body 40 also includes thin annular section 48 to further define chamber 17. A second cylindrical through bore 45 is provided parallel to and axially spaced from bore 44. Steel tube 50 is tightly fitted in bore 45 and forms part of the exhaust refrigerant flow passageway in communication with the enlarged chamber 17 and exhaust flow channel 24. Tube 50 will be connected to suitable tubing to return the used refrigerant to a retrieval vessel or to atmosphere. Appropriate connectors and tubing/hoses for connecting to tube 50, tube 22 and thermocouple pins are shown, for example, in the aforementioned Rubinsky, et al. application. A third through bore 46 receives a thermocouple pin 52 which in conjunction with a second thermocouple (not shown) located, for example, at the upstream region of tube section 28 proximate end wall (e.g., washer) 65, and/or at or near the outlet 23 of $LN_2$ supply tube, and/or at the probe shaft wall in freezing zone section 15, help monitor the tip temperature.

A cryoprobe instrument has been prepared as shown in FIG. 1. The outer shell 10 was formed using a 3.25 inch (82.55 mm) long, 1 inch (25.4 mm) diameter (O.D.) standard wall stainless steel tube for body portion 11, 5/8 inch (15.9 mm) (O.D.), 2.25 inch (57.2 mm) long standard wall stainless steel tube for intermediate section 12 and 7.25 inch (184 mm long), 3 millimeter O.D. thin wall stainless steel tube for the probe shaft 13. Exhaust flow tube section 32 was formed from thin wall stainless steel tube 10TW (0.187 inch O.D.) and small diameter section 34 was formed from stainless steel tube with an outside diameter of 0.082 inch and a wall thickness of 0.008 inch. The $LN_2$ supply tube 22 includes large diameter section 25 formed from 12TW (O.D.= 0.108–0.110 inch, wall thickness=0.009 inch) stainless steel tube and reduced diameter section 28 formed from 19 XTW (O.D.=0.0415–0.0425 inch, wall thickness=0.0035 inch) stainless steel tube. Vent hole 29 is drilled with a single filament wire drill to a diameter of 0.020 inch (0.508 mm) located in vacuum chamber 17. Holes 29a–d are drilled to a diameter of 0.010 inch (0.254 mm). Hollow chamber 17 is formed from a 5/8 inch threaded (NPT) cap. Vacuum chamber 30, with the assistance of zeolite particles 37 is evacuated to $10^{-7}$ mmHg. Teflon tape was wrapped around tube 34.

Using the structure described above, with sub-cooled liquid nitrogen at approximately −200° C. supplied at a pressure of 40 to 60 psi to the inlet of $LN_2$ supply tube 22 at a flow rate of approximately 0.25 liters per minute, the temperature at the probe tip can be reduced to and maintained at approximately −200° C. Moreover, a temperature of −206° C. can be achieved in as little time as 30 seconds. In comparison, a conventional cryoprobe having a probe tip diameter of 3 or 4 mm but without vent holes, cannot achieve temperatures as low as −196° C..

Figure 9:
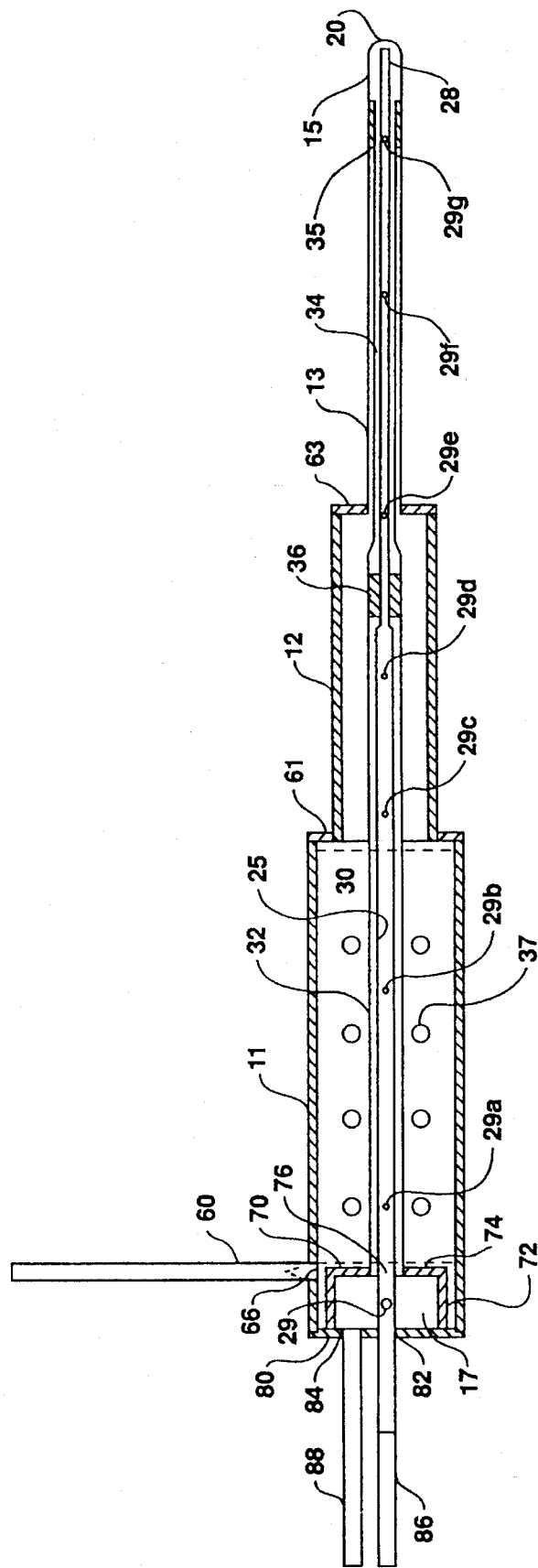
FIG. 9 is a schematic side elevation view of a modified embodiment of a cryosurgical probe according to the invention.

FIG. 9 illustrates a modified embodiment of the vented cryosurgical probe according to the invention. As shown in FIG. 9 the large diameter section 32 of the exhaust flow channel extends further beyond the larger diameter section 25 and insert elements 35, 36 help to center small diameter section 28 of the supply tube within small diameter section 34 of the exhaust flow channel and reduce the likelihood that the walls of the supply tube and exhaust tube will contact each other, even when the probe is caused to bend when inserted into a patient.

In FIG. 9, hollow chamber 17 is formed by cup member 70 which includes cylindrical side wall portion 72 and bottom wall portion 74. Bottom wall portion 74 includes a central aperture 76 of the same or slightly smaller diameter than tube 32 to fluid tightly receive the latter. Probe wall end piece or cover 80 is fixed to probe body portion 11 and to the top edge of side wall portion 72, for example by welding. Cover 80 includes central aperture 82 for fluid tightly receiving Teflon tubing connector 86 through which the inlet end of the supply tube section 25 is received and to which is connected the external $LN_2$ refrigerant supply line (not shown). A second aperture 84 in cover 80 fluid tightly receives one end of Teflon tubing connector 88, the opposed end of tube 88 being connected to the external refrigerant return tubing (not shown). A particularly preferred external insulated transport hose containing the external $LN_2$ refrigerant supply line and return tubing is described in the commonly assigned, co-pending application Ser. No. 08/087,289, filed Jul. 8, 1993, the disclosure of which is incorporated herein in its entirety by reference thereto.

As previously described copper tube 60 is used to evacuate vacuum chamber 30 and is then sealed as by pinching the side of the tube together near the casing 11, as schematically shown in phantom lines.

In this construction, rearwardmost ventilation hole 29 in chamber 17 may have a diameter of about 0.025 inch, and seven smaller ventilation holes 29a, 29b, 29c, 29d, 29e, 29f, and 29g are shown substantially equally spaced along the length of the exhaust tube sections 25 and 28. For example, for a cryoprobe supply tube 14 inches long, with a probe shaft 13 of about 6 to 7 inches in length, the smaller holes may be about 0.010–0.014 inch diameter and spaced apart about 1.5 inches.

Figure 10:
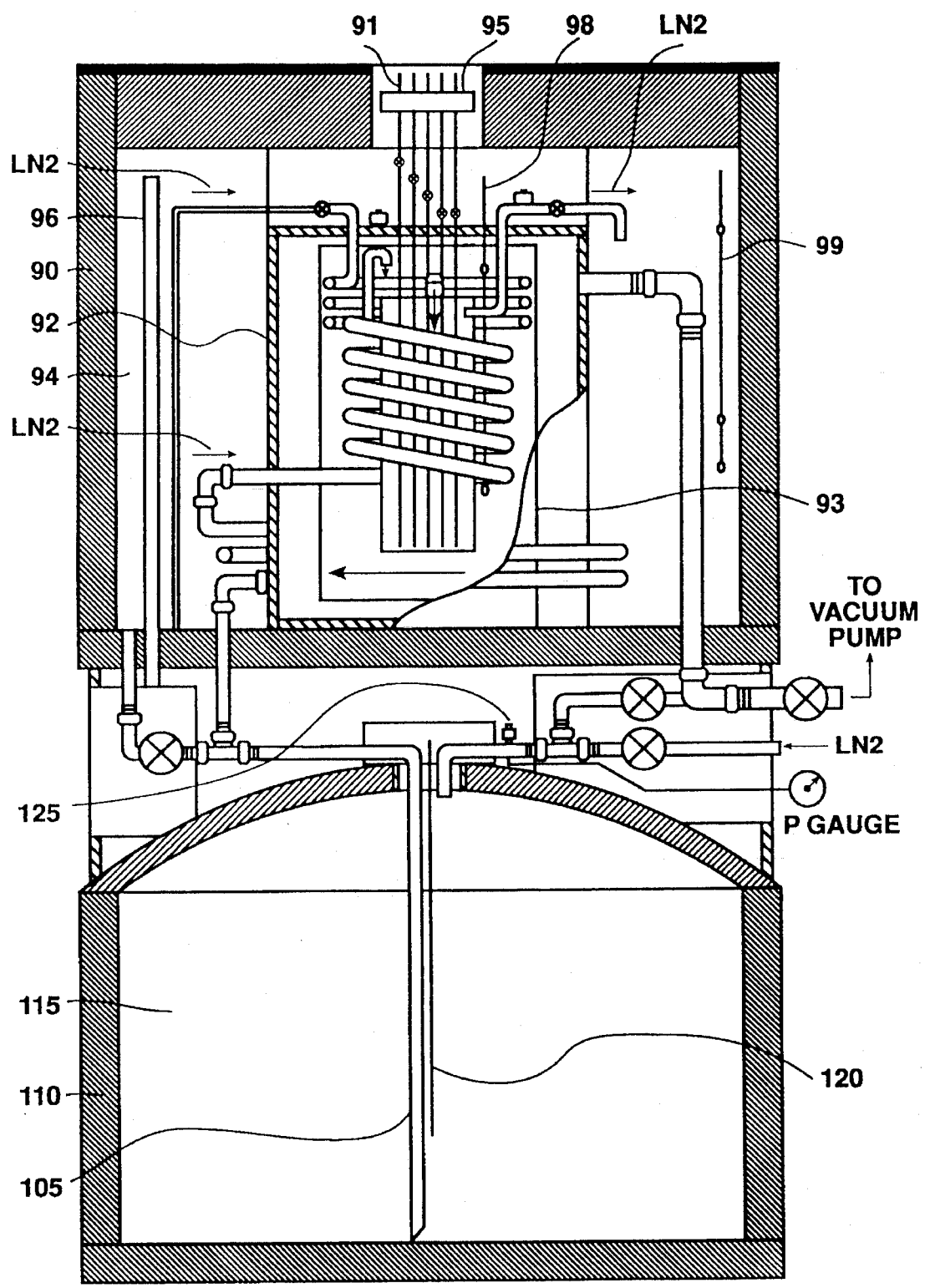
FIG. 10 is a schematic side elevation view, partially in section, of a sub-cooling system for use with the present invention.

A sub-cooling system using two vertically arranged dewars, each of 80 liters capacity, is schematically illustrated in FIG. 10. The upper dewar 90 includes the slush chamber 92 while lower chamber 110 is the supply and retrieval vessel for receiving pressurized $LN_2$ for driving the system as well as for receiving return refrigerant (usually a liquid/gas mixture).

$LN_2$ in the main chamber 94 of dewar 90 flows to dewar 110 via drain line 105. Nitrogen gas vapors generated in chamber 115 of lower dewar 110 enter the upper dewar chamber 94 via exhaust line 96. The operation of slush chamber 92 is substantially as described in the aforementioned Rubinsky, et al. application, the disclosure of which is incorporated herein by reference thereto.

The amount of $LN_2$ present in chamber 115 can be measured by $LN_2$ sensor 120 and the pressure adjusted by safety valve 125 designed to maintain pressure at or below 80 psi, for example.

Upper dewar 90 is shown with five $LN_2$ probe supply lines 91 which extend to the bottom of slush chamber vessel 93. A heater block 95 may be provided to warm the $LN_2$ flowing to the probes, for example, at the conclusion of the freezing cycle to allow removal of the probe(s) from the frozen tissue.

The structures described above are capable of forming an ice ball as large as 40 mm in diameter within 20 minutes of operation. Furthermore, for a cryosurgical probe with the same dimensions of the cryogen supply tube and cryogen return tube but with a probe shaft diameter of 6 millimeters an ice ball as large as 70 to 75 millimeters (approximately 3 inches) can be obtained. With currently available cryoprobes a probe shaft diameter of at least 9 millimeters is required to obtain an ice ball of near these dimensions. The length of the ice ball varies with the length of the probe tip.

It is understood that reference to "ice ball" is to the insertion of the cryoprobe tip in water, rather than in living tissue or a tumor. Nevertheless, the size of an ice ball formed in water is indicative of the extent of cooling when the same probe tip is used under the same conditions (e.g., cryogen temperature, flow rate and pressure) in a surgical procedure to destroy living tissue.

A prototype system using the cryoprobe instrument substantially as illustrated in FIG. 9 has been used in the treatment of more than 100 prostate cancers, 26 liver cancers, five lung cancers, two brain cancers and one eye cancer since October 1991.

This device, which used super-cooled liquid nitrogen circulating through its tip, froze the tumor to −30° F. in about 15 minutes. Upon completion of the procedure the device is withdrawn and the body absorbed the dead tissue over time. Surgeons have used up to five separate probes simultaneously to destroy large or multiple tumors.

Referential Example

Figure 11:
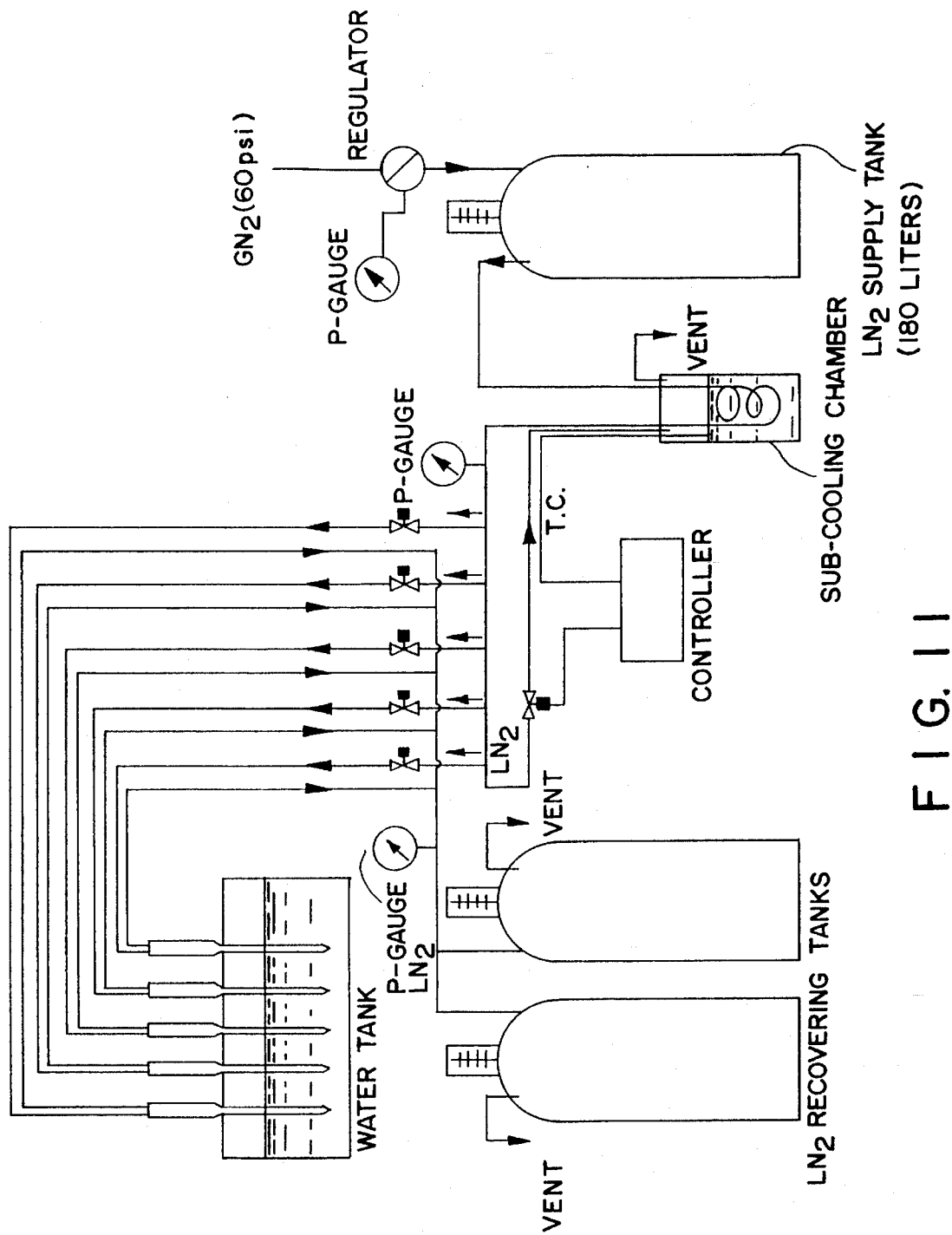
FIG. 11 is a schematic flow diagram of a testing station used to test up to 5 cryoprobes according to the invention.
Figure 12:
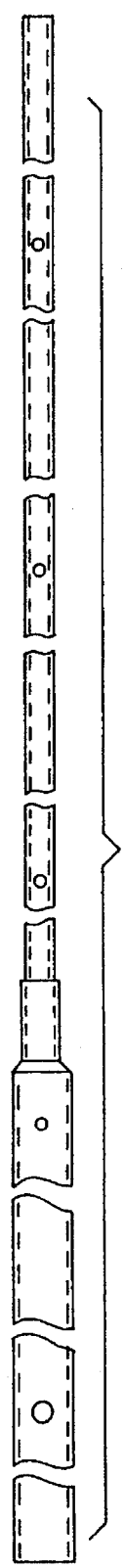
FIG. 12 is a side view, partially broken, of an $LN_2$ supply tube according to an embodiment of the invention.

Using the testing station illustrated in FIG. 11, a series of 3 millimeter probes having the construction shown in FIG. 1 with a supply tube 14 inches (35.56 cm) long (0.07" O.D. in upstream section and 0.036" O.D. downstream section) were tested with different hole patterns in the supply tube. The large hole had a diameter of 0.05 or 0.025 inch and the small hole(s) had a diameter of 0.0100–0.0130 inch, unless otherwise noted. The test probes were vacuum laser welded. Each pattern was tested with 5 cryoprobes and the tests were repeated 3 or 4 time on the test station. The water temperature in the water tank was set at either 17° C. or 27° C. without any type of convection barrier. The general configuration of a typical supply tube used in these experiments is shown in FIG. 12 (Pattern 1B4S, #5).

In Tables I–IV, the hole spacings for the different probe patterns were as follows:

| Pattern (#) | Big hole | Small Holes |
|---|---|---|
| 0B7S (3) | — | 2 holes 1.5 inches apart at downstream end of large section; 5 holes 1.5 inches apart starting 1 inch from outlet |
| 0B5S (6) | — | 5 holes 1.5 inches apart starting 1 inch from outlet |
| 0B8S (2) | — | 3 holes 1.5 inches apart starting near downstream end of large section; 5 holes 1.5 inches apart starting 1 inch from outlet |
| 1B0S (9) | 1 @ 0.05" | — |
| 1B2S (8) | 1 @ 0.025" | 1 hole 1 inch from outlet; 1 hole 6 inches from outlet |
| 1B3S (7) | 1 @ 0.025" | 3 holes 1.5 inches apart starting 1 inch from outlet |
| 1B4S (5) | 1 @ 0.025" | 3 holes 2 inches apart starting 1 inch from outlet; 1 hole in large section at 2.25 inches downstream from big hole |
| 1B5S (4) | 1 @ 0.025" | 5 holes 1.5 inches apart starting 1 inch from outlet |
| 1B7S (1) | 1 @ 0.025" | 5 holes 1.5 inches apart starting 1 inch from outlet; 2 holes equally spaced at 1.5 inches apart starting 1.5 inches downstream of big hole |

The following parameters were recorded: 1) the external probe tip temperature, approximately in the middle of the freeze zone; b) the regular probe temperature; c) the rate of nitrogen consumption, and d) the diameter and length of ice ball at the end of 15 minutes test.

Table 1 summarizes the results obtained from the test station with a water tank temperature of 17° C. The supply tube pattern is represented by xByS, where x stands for the number of big hole(s) (e.g., 0.025") positioned in the $LN_2$ return chamber and y the number of small holes along the supply tube. $LN_2$ usage is the total consumption of $LN_2$ for 5 cryoprobes over a period of 15 minutes in volume (liters). Flow rate (liter/min. Probe) represents the volume of liquid nitrogen flowing through each probe per minute. All three parameters are actually variables in time. The precooling characteristics of each probe was measured for the times to reach the following four critical temperatures: a) −70° C.: the regular probe temperature used for the "sticking mode" in prostate cryosurgery; b) 0° C.: the external probe tip temperature representing the equilibrium freezing temperature of pure water; c) −30° C.: the external probe tip temperature representing the threshold where massive ice crystallization occurs, which may in effect vary between −25° C. and 35° C. ; and d) the temperature at which the external probe tip temperature reveals a drastic decline ("kicking out") representing the threshold where liquid is capable of reaching the probe tip and maximum heat transfer efficiency is attained thereafter. The minimum external probe tip temperature is represented by Table II summarizes the results obtained with the test station of FIG. 11 with a water tank temperature of 27° C. In general, the results are similar to those presented in Table I.

Table III summarizes the results obtained for the inventive cryosurgical probe using the Assignee's commercially available AccuProbe® system at Allegheny General Hospital, Pittsburgh, Pa., with a water tank temperature of 27° C. The codes for each pattern are similar to those used in Tables I and II except that B* stands for a big hole of 0.020" in the return chamber and S* small hole of 0.007" along the small diameter downstream portion of the supply tube. The pattern 1B2S* performed better than the other patterns in terms of the nitrogen consumption, ice ball size, cool-down characteristics and minimum temperature.

Table IV summarizes the results obtained using the AccuProbe® system in Allegheny General Hospital with a water tank temperature of 17° C. Only pattern 1B2S* was tested at this temperature. The probes that passed the previous test were used in this case.

The experiments generally demonstrate that multiple holes along the supply tube are necessary to keep a steady liquid flow to the probe tip. The size of these smaller (mini) holes preferably does not exceed 0.010" in diameter.

Both experimental and preliminary clinical results have demonstrated that the best vent hole pattern in a 3 millimeter probe among those patterns that have been tested so far is 1B2S*, with one hole of 0.025" in the return chamber and two holes of 0.007" on the downstream (1B2S*) of the supply tube. The 1B2S* 3 mm cryoprobe offers the following advantages over conventional 3 millimeter cryoprobes.

a) The ice ball size is at least 37% larger in diameter or 156% larger in volume.

b) The total nitrogen consumption is predicted to be approximately 25% less.

c) The external probe tip temperature is at least 70° C. lower.

d) The probe performance is more uniform in terms of ice ball size, cool-down characteristics and attainable minimum temperature.

e) The manufacturing cost for each supply tube is reduced. While specific embodiments of the invention have been described in detail, however, it should be understood that the present invention may be varied and modified without departing from the scope of the invention.

TABLE I

| PROBE PATTERN | LN$_2$ USAGE (Liters) | FLOW RATE Liter/Min. Prob. | ICE BALL Dia. (CM) × Length (CM) | COOL-DOWN TIME (min.) | | | | T min (°C.) |
|---|---|---|---|---|---|---|---|---|
| | | | | −70° C. (P) | 0° C. (T) | −30° C. (T) | Kicking | |
| 0B0S (#10) | 17.4 ± 0.8 | 0.23 ± 0.01 | 2.6 ± 0.5 × 4.0 ± 0.2 | 5.2 ± 0.7 | 3.7 ± 0.9 | 5.2 ± 0.9 | α | −98.8 ± 34.4 |
| 0B5S (#6) | 27.1 ± 3.2 | 0.36 ± 0.04 | 2.7 ± 0.4 × 4.4 ± 0.6 | 2.6 ± 0.7 | 1.7 ± 0.4 | 2.9 ± 0.8 | 10.2 ± 2.5 (30 ± 22%) | −107.9 ± 30.5 |
| 0B7S (#3) | 31.0 ± 0.70 | 0.42 ± 0.01 | 3.2 ± 0.4 × 4.3 ± 0.3 | 2.3 ± 0.4 | 1.7 ± 0.4 | 2.4 ± 0.5 | 7.2 ± 3.7 (81 ± 10%) | −150.3 ± 20.2 |
| 0B8S (#2) | 35.0 ± 1.80 | 0.47 ± 0.03 | 3.0 ± 0.4 × 4.4 ± 0.6 | 3.0 ± 0.7 | 1.8 ± 0.5 | 2.7 ± 0.9 | 7.7 ± 2.7 (67 ± 12%) | −119.2 ± 25.7 |
| 1B0S (#9) | 36.8 | 0.49 | 3.1 ± 0.4 × 4.2 ± 0.2 | 2.0 ± 0.4 | 1.6 ± 0.1 | 2.2 ± 0.4 | 5.2 ± 1.0 (50%) | −143.7 ± 30.9 |
| 1B2S (#8) | 40.5 ± 1.4 | 0.54 ± 0.02 | 3.3 ± 0.3 × 4.3 ± 0.3 | 2.0 ± 0.5 | 1.3 ± 0.3 | 1.6 ± 0.2 | 3.9 ± 0.3 (100%) | −158.6 ± 7.4 |
| 1B3S (#7) | 42.2 ± 1.5 | 0.56 ± 0.02 | 3.0 ± 0.5 × 4.5 ± 0.7 | 1.5 ± 2.3 | 1.0 ± 0.1 | 1.7 ± 0.5 | 5.3 ± 2.3 (40%) | −136.3 ± 29.3 |
| 1B4S (#5) | 44.7 ± 1.4 | 0.60 ± 0.02 | 2.7 ± 0.4 × 4.2 ± 0.4 | 1.3 ± 0.4 | 1.1 ± 0.3 | 1.6 ± 0.3 | 4.1 ± 0.02 (20%) | −105.2 ± 33.1 |
| 1B5S (#4) | 47.4 ± 2.2 | 0.63 ± 0.03 | 2.4 ± 0.5 × 3.7 ± 0.6 | 1.4 ± 0.3 | 1.0 ± 0.3 | 1.5 ± 0.2 | 5.5 ± 0.8 (40%) | −123.9 ± 32.3 |
| 1B7S (#1) | 57.1 ± 2.2 | 0.76 ± 0.03 | 2.1 ± 0.2 × 4.0 ± 0.7 | 1.1 ± 0.3 | 0.8 ± 0.1 | 2.0 ± 0.5 | α (0%) | −70.3 ± 11.5 |
| 1B7S (#1A) | 56.5 ± 2.0 | 0.75 ± 0.03 | 2.6 ± 0.3 × 4.2 ± 0.2 | 1.2 ± 0.2 | 1.1 ± 0.1 | 2.8 ± 0.5 | α (0%) | 46.9 ± 7.1 |

NOTE:
PROBE PATTERN #'s 1–10 were manufactured by Sharon Vacuum Inc.
PROBE PATTERN # 1A was manufactured by QSI.

TABLE II

| PROBE PATTERN | LN$_2$ USAGE (Liters) | FLOW RATE Liter/Min. Prob. | ICE BALL Dia. (CM) × Length (CM) | COOL-DOWN TIME (min.) | | | | T min (°C.) |
|---|---|---|---|---|---|---|---|---|
| | | | | −70° C. (P) | 0° C. (T) | −30° C. (T) | Kicking | |
| 0B0S (#10) | 17.1 ± 1.4 | 0.23 ± 0.02 | 1.6 ± 0.2 × 3.3 ± 0.2 | 5.7 ± 1.1 | 4.9 ± 0.9 | 6.4 ± 1.4 | α | −80.1 ± 28.4 |
| 0B7S (#3) | 43.4 ± 3.1 | 0.58 ± 0.04 | 1.8 ± 0.5 × 3.2 ± 0.3 | 1.88 ± 0.6 | 1.2 ± 0.1 | 1.6 ± 0.4 | 2.9 ± 0.3 (60%) | −123.1 ± 38.1 |
| 1B0S (#9) | 33.5 ± 4.4 | 0.35 ± 0.12 | 2.1 ± 0.3 × 3.4 ± 0.2 | 2.7 ± 0.7 | 2.0 ± 0.6 | 3.5 ± 2.3 | 5.5 ± 1.0 (60 ± 35%) | −137.7 ± 38.1 |
| 1B2S (#8) | 40.8 | 0.51 | 2.2 ± 0.3 | 1.6 | 1.6 | 2.5 | 9.0 ± 3.0 | −145.0 |

TABLE II-continued

| PROBE PATTERN | LN₂ USAGE (Liters) | FLOW RATE Liter/Min. Prob. | ICE BALL Dia. (CM) × Length (CM) | COOL-DOWN TIME (min.) −70° C. (P) | 0° C. (T) | −30° C. (T) | Kicking | T min (°C.) |
|---|---|---|---|---|---|---|---|---|
|  | ± 1.4 | ± 0.02 | × 3.4 ± 0.2 | ± 0.3 | ± 0.4 | ± 0.7 | (86 ± 9%) | ± 24.0 |
| 1B7S (#1) | 52.8 ± 4.4 | 0.70 ± 0.06 | 1.2 ± 0.1 × 3.4 ± 0.5 | 1.1 ± 0.2 | 1.1 ± 0.3 | 3.9 ± 2.2 | α | −49.5 ± 16.0 |
| 1B7S (#1A) | 54.2 ± 0.7 | 0.72 ± 0.01 | 1.4 ± 0.3 × 3.4 ± 0.3 | 1.1 ± 0.2 | 1.3 ± 0.2 | 4.4 ± 0.7 | α | −31.3 ± 5.1 |

TABLE III

| PROBE PATTERN | LN₂ USAGE (Liters) | FLOW RATE Liter/Min. Prob. | ICE BALL Dia. (CM) × Length (CM) | COOL-DOWN TIME (min.) −70° C. (P) | 0° C. (T) | −30° C. (T) | Kicking | T min (°C.) |
|---|---|---|---|---|---|---|---|---|
| 0B5S (#6) | (76–44) = 32% | 0.34 | 1.7 ± 0.6 × 3.6 ± 0.4 | 5.0 ± 1.7 | 4.1 ± 0.9 | 9.7 ± 2.9 | α | −57.2 ± 44.9 |
| 0B7S (#3) | (96–62) = 34% | 0.37 | 2.3 ± 0.5 × 4.3 ± 0.5 | 2.5 ± 0.5 | 2.5 ± 0.5 | 6.4 ± 1.3 | 10.8 ± 0.7 (66%) | −108.2 ± 47.4 |
| 0B8S (#2) | (98–52) = 46% | 0.49 | 2.2 ± 0.4 × 3.7 ± 0.4 | 2.9 ± 1.3 | 2.4 ± 0.8 | 6.6 ± 3.2 | 7.7 ± 1.6 (50%) | −90.4 ± 49.2 |
| 1B0S (#9) | (78–0) = 78% | 0.83 | 2.0 ± 0.3 × 3.7 ± 0.2 | 1.3 ± 0.1 | 3.1 ± 1.1 | 7.8 ± 4.1 | 12.3 ± 1.4 (75%) | −107.0 ± 44.6 |
| 1B2S (#8) | (100–50) = 50% | 0.53 | 1.9 ± 0.4 × 3.7 ± 0.1 | 1.2 ± 0.5 | 1.9 ± 0.5 | 5.2 ± 4.1 | 13.5 (25%) | −74.2 ± 27.8 |
| 1B7S (#1) | (100–40) = 60% | 0.64 | 1.9 ± 0.4 × 3.5 ± 0.3 | 1.2 ± 0.12 | 1.9 ± 1.0 | 4.5 ± 1.0 | α | −54.2 ± 13.1 |
| 1B5S* (#11) | (100–40) = 60% | 0.64 | 2.1 ± 0.1 × 3.9 ± 0.1 | 2.1 ± 0.23 | 1.8 ± 0.2 | 3.4 ± 0.6 | α | −60.5 ± 14.8 |
| 1B2S* (#12) | (98–70) = 28% (100–72) = 28% | 0.30 | 2.6 ± 0.2 × 4.2 ± 0.1 | 1.9 ± 0.3 | 1.8 ± 0.2 | 3.7 ± 0.5 | 6.0 ± 1.9 (75%) | −126.5 ± 40.0 |

NOTE: PROBE PATTERN #'s 11 and 12 were manufactured by Sharon Vacuum Inc.

TABLE IV

| PROBE PATTERN | LN₂ USAGE (Liters) | FLOW RATE Liter/Min. Prob. | ICE BALL Dia. (CM) × Length (CM) | COOL-DOWN TIME (min.) −70° C. (P) | 0° C. (T) | −30° C. (T) | Kicking | T min (°C.) |
|---|---|---|---|---|---|---|---|---|
| 1B2S* (#12) |  |  | 3.7 ± 0.1 × 5.0 ± 0.1 | 1.5 ± 0.3 | 1.3 ± 0.3 | 2.7 ± 0.8 | (100%) 5.2 ± 2.1 | −149.0 ± 8.1 |

What is claimed is:

1. A method for producing sub-freezing temperatures sufficiently low to destroy living tissue by supplying a cryogenic liquid through an insulated passageway to a closed highly temperature conductive tip at the end of the passageway, said method comprising:

providing a stream of pressurized cryogenic liquid refrigerant from a supply thereof through a first flow passageway to an outlet terminating in the vicinity of but spaced from the closed tip, said flow passageway including vent means along the length thereof, causing the cryogenic refrigerant to flow in countercurrent flow from the closed tip in an annular second flow passageway surrounding said first flow passageway, and providing thermal insulation for the refrigerant flowing through the second flow passageway and extending longitudinally beyond said vent means, whereby gas initially present in the first flow passageway is vented through said vent means into the second flow passageway, and any vaporized liquid cryogen flowing through the first passageway can be vented into the second flow passageway, said vent means comprising at least one through opening having a diameter small than the diameter of the outlet of the first flow passageway, said diameter being sufficient to allow a portion of the cryogenic liquid to be vented from said first passageway to said second passageway, whereby bubbling of the cryogenic liquid in the first flow passageway which would impede flow of liquid therethrough is effectively inhibited, and the temperature differential between the liquid cryogen flowing through the first flow passageway and the counter-current flowing refrigerant in the second flow passageway is reduced.

2. The method of claim 1, wherein said pressurized cryogenic liquid comprises sub-cooled liquid nitrogen.

3. In a cryoprobe instrument including a probe casing having a closed distal end including a freezing zone for freezing live tissue and a proximal end for receiving liquid cryogenic refrigerant from an external source thereof, a cryogenic refrigerant supply tube having a supply tube inlet for receiving liquid cryogenic refrigerant at the proximal end and a supply tube outlet for delivering liquid cryogenic refrigerant from the proximal end to the freezing zone at the closed end, a cryogenic refrigerant exhaust channel surrounding the supply tube for transporting the used refrigerant from the closed end towards the proximal end, said exhaust channel having an exhaust channel inlet, and thermal insulation for insulating the side wall of the probe casing from the exhaust channel inlet to the proximal end, the improvement comprising vent means in the supply tube upstream of said freezing zone and located between the exhaust channel inlet and the supply tube inlet and in flow communication with the thermally insulated exhaust channel, thereby enabling during operation of the cryoprobe instrument gas formed or present in the supply tube to be vented to the exhaust channel.

4. The cryoprobe instrument of claim 1, wherein the vent means comprises a plurality of vent holes, longitudinally spaced along the supply tube, the rearwardmost vent hole having a diameter of from about 0.008 to 0.030 inches and wherein, each of the remaining vent holes is of smaller diameter in the range of from about 0.004 to 0.010 inches.

5. The cryoprobe instrument of claim 4 wherein the probe casing comprises an enlarged diameter handle portion at the proximal end thereof remote from the closed end, and a smaller diameter shaft portion including the closed end thereof; wherein the shaft portion has a diameter of from about 2.5 to 8 millimeters; wherein the exhaust channel comprises an enlarged diameter portion defining an exhaust chamber at the proximal end of the casing, a small diameter portion in the shaft portion and an intermediate diameter portion connecting the enlarged diameter portion to the small diameter portion; wherein the supply tube comprises a small diameter portion in the shaft portion of the casing and a larger diameter portion extending from the small diameter portion to beyond the proximal end of the casing, thereby providing a larger annular exhaust flow passageway in the handle portion than in the probe shaft portion; and wherein the rearwardmost hole in the supply tube is located at a position communicating with said exhaust chamber.

6. The cryoprobe instrument of claim 5, wherein said thermal insulation comprises a sealed tubular vacuum chamber.

7. The cryoprobe instrument of claim 3, wherein said vent means comprises a plurality of longitudinal spaced holes, the axes of which are at an angle of from 20° to 80° with respect to the longitudinal axis of the supply tube.

8. The cryoprobe instrument of claim 3, wherein said vent means comprises a plurality of longitudinally spaced shrouded holes, said shrouds being formed by a portion of the supply tube at the forward edge of said holes overlying said holes.

9. The cryogenic instrument of claim 3, wherein said vent means comprises at least one elongated slot in said supply tube.

10. The cryoprobe instrument of claim 3, wherein said vent means comprises a porous sintered metal supply tube.

11. A cryosurgical instrument which comprises a hollow probe tip having a closed end forming a freezing zone for freezing live tissue, a first inlet for receiving cryogenic liquid refrigerant and a first outlet for removing cryogenic refrigerant, a refrigerant supply tube for transporting cryogenic liquid refrigerant from the first inlet to the probe tip, said supply tube having ventilation means which prevents the free flow of refrigerant therethrough while allowing the ventilation of any gas present in the supply tube, an exhaust flow tube for transporting refrigerant from the freezing zone to the first outlet, wherein the supply tube and exhaust flow tube are arranged as concentric inner and outer tubes, with the supply tube forming the inner tube and extending beyond the outer tube in the freezing zone, and a thermal insulation chamber surrounding said concentric tubes and extending to the freezing zone, whereby the ventilation means is located upstream of said freezing zone and allows ventilation of any gas formed in the supply tube so as to maintain a high flow rate of refrigerant through the supply tube and to decrease the extent of counter-current heat exchange between the cryogenic refrigerant in the supply tube and the exhaust flow tube by allowing liquid refrigerant to vent to the exhaust flow tube and thereby cool the cryogenic refrigerant flowing through the exhaust tube.

12. A cryoprobe instrument comprising a handle portion, a shaft portion of smaller diameter than the handle portion extending from the handle portion and terminating at its distal end with a closed tip providing a freezing zone effective during operation of the instrument to freeze living tissue when in contact therewith, a liquid cryogenic refrigerant supply passageway extending through the handle portion and through the shaft portion, said supply passageway having an inlet end extending proximally of said handle portion and an outlet end for supplying cryogenic refrigerant to the freezing zone at the closed tip of said shaft portion, a cryogenic refrigerant return passageway, said return passageway having an inlet for receiving cryogenic refrigerant from the freezing zone and an enlarged chamber within the handle portion, said shaft portion being thermally insulated to inhibit ice formation on the outer surface of the shaft portion other than in the freezing zone, and vent means in the supply passageway for enabling during operation of the cryoprobe instrument gas formed or present in the supply passageway to be vented to the return passageway, said vent means comprising at least one aperture located within the enlarged chamber of the return passageway.

13. The cryoprobe instrument of claim 12 wherein the shaft portion has a diameter of from about 2.5 millimeters to about 4 millimeters.

14. The cryoprobe instrument of claim 13 wherein the vent means further comprises from 2 to about 6 longitudinally spaced apertures in the supply passageway, said longitudinally spaced apertures being located distally of the enlarged chamber and proximally of the inlet to the cryogenic refrigerant return passageway, and wherein the diameter of each of the longitudinally spaced apertures is smaller than the diameter of the aperture located in the enlarged chamber.

15. The cryoprobe instrument of claim 14 wherein the diameter of the aperture located in the enlarged chamber is in the range of from about 0.015 inch to about 0.028 inch and the diameters of the longitudinally spaced apertures are from about 0.004 inch to about 0.014 inch.

16. The cryoprobe instrument of claim 12 further comprising connector means fluid tightly connectable at one end thereof to the proximal end of said handle portion and at the opposed end thereof fluid tightly connectable to delivery tubing for delivering liquid cryogenic refrigerant from an external supply, said connector means including a through passageway extending longitudinally therethrough, whereby upon fitting the connector means to the handle portion the supply tube extends into and through said through passageway.

17. A cryoprobe instrument comprising a handle portion, a shaft portion of smaller diameter than the handle portion extending from the handle portion and terminating at its distal end with a closed tip providing a freezing zone effective during operation of the instrument to freeze living tissue when in contact therewith, a liquid cryogenic refrigerant supply passageway extending through the handle portion and through the shaft portion, said supply passageway having an inlet end extending proximally of said handle portion and an outlet end for supplying cryogenic refrigerant to the freezing zone at the closed tip of said shaft portion, a cryogenic refrigerant return passageway surrounding the supply passageway, said return passageway having an inlet for receiving cryogenic refrigerant from the freezing zone and an enlarged chamber within the handle portion, said shaft portion being thermally insulated to inhibit ice formation on the outer surface of the shaft portion other than in the freezing zone, and vent means in the supply passageway for enabling during operation of the cryoprobe instrument gas formed or present in the supply passageway to be vented to the return passageway, said vent means comprising a plurality of from about 2 to about 8 longitudinally spaced apertures in the supply passageway, said apertures being located dietally of the enlarged chamber and proximally of the freezing zone.

18. The cryoprobe instrument of claim 17 wherein the shaft portion has a diameter of from about 2.5 millimeters to about 4 millimeters.

19. The cryoprobe instrument of claim 17 further comprising an aperture in the enlarged chamber of the supply passageway, said aperture having a diameter which is from about 1.5 to about 2.5 times larger than the diameter of said longitudinally spaced apertures.

20. The cryoprobe instrument of claim 19 wherein the axes of the longitudinally spaced holes are at an angle of from about 30° to 70° with respect to the longitudinal axis of the supply passageway.

21. In a cryoprobe instrument including a probe casing having a closed distal end forming a freezing zone for freezing live tissue and a handle portion at the proximal end, thereon cryogenic refrigerant supply passageway for transporting liquid cryogenic refrigerant from the proximal end to the freezing zone, a cryogenic refrigerant exhaust channel for transporting the used refrigerant from the freezing zone towards the proximal end, and thermal insulation for insulating the side wall of the probe casing from the freezing zone towards the proximal end, the improvement comprising vent means in at least the portion of the supply passageway surrounded by the thermal insulation and within the handle portion of the probe casing thereby enabling during operation gas formed or present in the supply passageway to be vented to the exhaust channel.

22. The improved cryoprobe instrument of claim 21 wherein the vent means comprises a plurality of vent holes, longitudinally spaced along the portion of the supply passageway surrounded by the thermal insulation.

* * * * *